United States Patent
Katsurada et al.

(10) Patent No.: US 10,136,905 B2
(45) Date of Patent: Nov. 27, 2018

(54) BALLOON CATHETER

(71) Applicant: ASAHI INTECC CO., LTD., Nagoya-shi, Aichi (JP)

(72) Inventors: Takeharu Katsurada, Nagoya (JP); Yuta Kubo, Seto (JP); Moritaka Ogido, Seto (JP)

(73) Assignee: ASAHI INTECC CO., LTD., Nagoya-shi (JP)

( * ) Notice: Subject to any disclaimer, the term of this patent is extended or adjusted under 35 U.S.C. 154(b) by 67 days.

(21) Appl. No.: 15/198,260

(22) Filed: Jun. 30, 2016

(65) Prior Publication Data
US 2017/0071613 A1 Mar. 16, 2017

(30) Foreign Application Priority Data
Sep. 15, 2015 (JP) .................. 2015-181288

(51) Int. Cl.
*A61M 29/00* (2006.01)
*A61B 17/22* (2006.01)
*A61M 25/10* (2013.01)

(52) U.S. Cl.
CPC .......... *A61B 17/22* (2013.01); *A61M 25/104* (2013.01); *A61M 25/1006* (2013.01); *A61M 25/1034* (2013.01); *A61M 25/1036* (2013.01); *A61B 2017/22001* (2013.01); *A61B 2017/22051* (2013.01); *A61M 2025/1093* (2013.01)

(58) Field of Classification Search
CPC .. A61M 2025/1093; A61M 2025/0081; A61M 25/0069; A61M 25/10; A61M 25/001; A61M 25/1006; A61M 25/0054; A61M 25/1025; A61M 25/1027; A61M 25/1034; A61M 25/104; A61F 2/958
See application file for complete search history.

(56) References Cited

U.S. PATENT DOCUMENTS 5,338,299 A * 8/1994 Barlow ............... A61M 25/104
604/103
5,429,605 A * 7/1995 Richling ........... A61M 25/1006
604/103.11
(Continued)

FOREIGN PATENT DOCUMENTS

EP   1 683 540 A1   7/2006
JP   H10-509057 A   9/1998
(Continued)

OTHER PUBLICATIONS

Jan. 19, 2017 Search Report issued in European Patent Application No. 16178087.9.
(Continued)

*Primary Examiner* — Elizabeth Houston
*Assistant Examiner* — Mohamed Gabr
(74) *Attorney, Agent, or Firm* — Oliff PLC

(57) ABSTRACT

A balloon catheter prevents detachment of a balloon from an inner shaft without using a conventional sleeve or heat-shrinkable tube. The balloon catheter includes a balloon, an inner shaft, and a tip having a proximal end portion that covers an outer periphery of a distal end of the balloon. The distal end of the balloon is sandwiched between the inner shaft and the proximal end portion of the tip, thereby joining the distal end of the balloon to the inner shaft and the tip.

4 Claims, 5 Drawing Sheets

(56) References Cited

U.S. PATENT DOCUMENTS

| | | |
|---|---|---|
| 6,918,920 B1 | 7/2005 | Wang et al. |
| 7,465,311 B2 | 12/2008 | Wang et al. |
| 8,221,444 B2 | 7/2012 | Wang et al. |
| 2002/0082549 A1 | 6/2002 | Duchamp |
| 2008/0004568 A1* | 1/2008 | Jeffrey ............... A61M 25/0069 |
| | | 604/96.01 |
| 2008/0077173 A1* | 3/2008 | Flanagan .......... A61M 25/1034 |
| | | 606/192 |
| 2012/0209176 A1 | 8/2012 | Anderson |
| 2015/0174364 A1* | 6/2015 | Kennelly ............ A61M 25/008 |
| | | 604/527 |

FOREIGN PATENT DOCUMENTS

| | | |
|---|---|---|
| JP | 2009-056297 A | 3/2009 |
| JP | 2012-096116 A | 5/2012 |
| JP | 2012-249811 A | 12/2012 |
| WO | 95/20417 A1 | 8/1995 |
| WO | 2013/166209 A1 | 11/2013 |

OTHER PUBLICATIONS

May 22, 2018 Office Action issued in Japanese Application No. 2015-181288.

* cited by examiner

BALLOON CATHETER

CROSS REFERENCE TO RELATED APPLICATION

This application claims priority to Japanese Application No. 2015-181288, which was filed on Sep. 15, 2015, the entire contents of which are incorporated herein by reference.

BACKGROUND

The disclosed embodiments relate to a medical device. Specifically, the disclosed embodiments relate to a balloon catheter to be inserted into a target site (such as a stenosis site) in a blood vessel in order to expand the target site.

Balloon catheters for expanding stenosis sites and the like have already been proposed. A balloon catheter mainly comprises a balloon as an inflatable body; an outer shaft joined to a proximal end of the balloon; and an inner shaft inserted into the inside of the balloon and the outer shaft. In the conventional balloon catheter, the balloon can be detached from the inner shaft or the outer shaft at a joining portion therebetween when the balloon is inflated. Various configurations have been proposed in order to solve this problem.

For example, U.S. Pat. No. 6,918,920 discloses a balloon catheter in which a distal tip is joined to a distal end of an inner tube; a proximal shaft portion of a balloon is joined to the inner tube; and the inner tube, the distal tip, and the proximal shaft portion of the balloon are joined by a sleeve.

Further, Japanese Patent Application Laid-Open No. 2009-056297 discloses a balloon catheter in which a proximal end of a balloon is sandwiched between a tube body and a heat-shrinkable tube.

However, in the foregoing balloon catheter according to U.S. Pat. No. 6,918,920, the proximal shaft portion of the balloon is merely joined to an outer periphery of the inner tube. Therefore, the balloon tends to detach from the inner tube when the balloon is inflated. Further, although the distal tip is joined to the distal end of the inner tube and an inner periphery of the sleeve, the joining strength is not enough. Therefore, disadvantageously, the distal tip also tends to break off from the inner tube. Specifically, when the internal pressure is increased in order to inflate the balloon, the proximal shaft portion of the balloon becomes susceptible to detachment from the inner tube. When the internal pressure is further increased, the balloon and the inner tube are forced to extend in the distal direction. This causes the sleeve to be pushed from the proximal end, which, in turn, makes the sleeve susceptible to detachment, and the distal tip may break off from the inner tube.

Furthermore, even if the foregoing heat-shrinkable tube disclosed in Japanese Patent Application Laid-Open No. 2009-056297 were used instead of the foregoing sleeve in U.S. Pat. No. 6,918,920, the distal tip might nonetheless break off from the inner shaft.

SUMMARY

Accordingly, an objective of the disclosed embodiments is to provide a balloon catheter in which a balloon is not easily detached from an inner shaft, and breakage and detachment of a tip from an inner shaft can be prevented without using the conventional sleeve or heat-shrinkable tube.

A balloon catheter of the disclosed embodiments comprises a balloon, an inner shaft joined to a distal end of the balloon, and a tip joined to a distal end of the inner shaft, wherein the tip extends in the proximal direction so as to cover an outer periphery of the balloon, and the distal end of the balloon, the inner shaft, and the tip are joined such that the distal end of the balloon is sandwiched between the inner shaft and a proximal end portion of the tip.

According to the aforementioned configuration, the distal end of the balloon, the inner shaft, and the tip are joined such that the distal end of the balloon is positioned at a portion sandwiched between the inner shaft and the proximal end portion of the tip. Therefore, the distal end of the balloon is not easily detached from the inner shaft. Further, since a conventional sleeve, heat-shrinkable tube, and the like are not used, the number of components can be reduced as a whole. Furthermore, the joining strength between the tip and the balloon can be optimized by adjusting the length and area of the balloon covered with the tip. Therefore, a risk of breakage and detachment of the tip from the inner shaft can certainly be reduced.

Additionally, a configuration is described herein where an outer periphery of the inner shaft has unevenness (i.e., an uneven surface topography) at a joining portion where the distal end of the balloon, the inner shaft, and the tip are joined. According to the aforementioned configuration, in a case where the unevenness is formed on the outer periphery of the inner shaft at a place facing the distal end of the balloon, the joining area between the distal end of the balloon and the outer periphery of the inner shaft can be increased. As a result, the distal end of the balloon is not easily detached from the inner shaft. For example, the distal end of the balloon is caught on the unevenness formed on the outer periphery of the inner shaft by virtue of an anchoring effect. Therefore, the distal end of the balloon is not easily detached from the inner shaft even when a high pressure is applied to the balloon.

A configuration is also described in which the unevenness on the outer periphery of the inner shaft is formed by burying a coil body inside the inner shaft. In a case where the unevenness is formed by the outer shape of the coil body as described above, an additional step of forming unevenness on the outer periphery of the inner shaft is not required. Therefore, the process for forming unevenness can be simplified.

Further, a configuration is described in which an inner periphery of the distal end of the balloon at the joining portion has unevenness corresponding to the unevenness of the outer periphery of the inner shaft. According to the aforementioned configuration, the joining area between the distal end of the balloon and the outer periphery of the inner shaft can be further increased. As a result, the distal end of the balloon is even more resistant to detachment from the inner shaft.

Advantageously, in the balloon catheter according to the disclosed embodiments, the balloon is not easily detached from the inner shaft, and breakage and detachment of the tip from the inner shaft can be prevented.

BRIEF DESCRIPTION OF THE DRAWINGS

FIG. 3B: an inner shaft; and FIG. 3C: a balloon).

DETAILED DESCRIPTION OF EMBODIMENTS

Balloon catheters according to the disclosed embodiments will be described in detail. However, the present invention shall not be limited to the embodiments described below, and modifications in design can be made appropriately. In FIGS. 1 to 5, the left side corresponds to the distal end, which is to be inserted into the body, and the right side corresponds to the proximal end, which is to be operated by an operator such as a physician.

Figure 1:
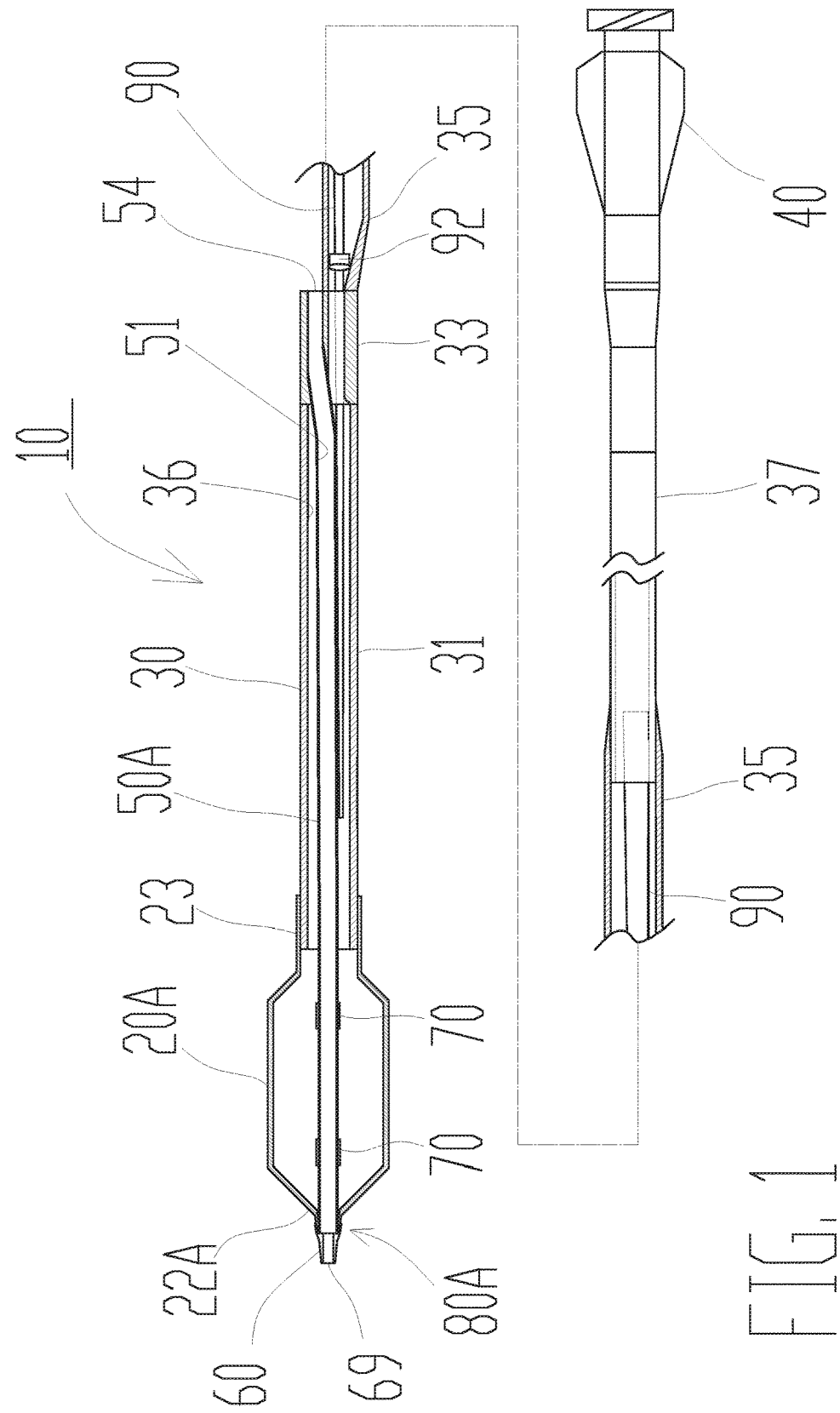
FIG. 1 shows a partial cross-sectional top view of a balloon catheter according to the disclosed embodiments.

For example, FIG. 1 shows a balloon catheter 10 that may be used for treating a stenosis site in a blood vessel of the heart, for example. The balloon catheter 10 comprises a balloon 20A, an outer shaft 30, a connector 40, an inner shaft 50A, a tip 60, and a core wire 90.

The balloon 20A functions to expand the stenosis site, and comprises a resin material. In addition, a distal end 22A of the balloon 20A is joined to a distal end of the inner shaft 50A and the tip 60, and a proximal end 23 of the balloon 20A is joined to a distal end of the outer shaft 30. Note that a joining structure of the distal end 22A of the balloon 20A will be described in more detail below.

The outer shaft 30 functions to supply a fluid to the balloon 20A, and comprises a tubular member constituting an inflation lumen 36 for supplying the fluid. Further, the outer shaft 30 has a distal end outer shaft portion 31, a guide wire port portion 33, a middle outer shaft portion 35, and a proximal end outer shaft portion 37 in that order from the distal end. The distal end outer shaft portion 31, the middle outer shaft portion 35, and the inner shaft 50A are joined at the guide wire port portion 33.

The inner shaft 50A is inserted into the distal end outer shaft portion 31, and the inflation lumen 36 is formed between the distal end outer shaft portion 31 and the inner shaft 50A. Further, the proximal end outer shaft portion 37 comprises a metal tubular member referred to as a so-called hypotube. In addition, a distal end of the proximal end outer shaft portion 37 is inserted into and joined to a proximal end of the middle outer shaft portion 35. Further, the connector 40 is attached to a proximal end of the proximal end outer shaft portion 37. Therefore, when a fluid for inflating the balloon 20A (such as a contrast agent and physiological saline) is supplied through an indeflator (not shown) to be attached to the connector 40, the fluid flows into the balloon 20A through the inflation lumen 36 to inflate the balloon 20A.

Note that the distal end outer shaft portion 31 and the middle outer shaft portion 35 are each preferably a tube comprising a resin such as a polyamide, polyamide elastomer, polyolefin, polyester, or polyester elastomer. Further, the proximal end outer shaft portion 37 preferably comprises stainless steel (SUS 304) or a superelastic alloy such as a Ni—Ti alloy.

The inner shaft 50A forms a guide wire lumen 51 for inserting a guide wire (not shown) thereinto. Further, a proximal end of the inner shaft 50A is joined to the guide wire port portion 33 of the outer shaft 30 to form a proximal end guide wire port 54. Furthermore, a distal end guide wire port 69 is formed at the tubular tip 60 arranged at the distal end of the inner shaft 50A.

Moreover, a marker member 70 having a cylindrical shape is arranged at an outer periphery of the inner shaft 50A in the inside of the balloon 20A.

The inner shaft 50A preferably comprises a resin such as a polyethylene, polyurethane, polyamide, polyamide elastomer, polyolefin, polyester, or polyester elastomer. The tip 60 is preferably formed with a soft resin such as polyurethane or polyurethane elastomer. Moreover, the marker member 70 preferably comprises a radiopaque metal material such as platinum or tungsten.

Further, the core wire 90 is attached to an inner periphery of the distal end of the proximal end outer shaft portion 37. The core wire 90 has a circular cross section, and is formed of a tapered metal wire material with a diameter that decreases toward the distal end. In addition, the core wire 90 extends through the middle outer shaft portion 35, the guide wire port portion 33, and the distal end outer shaft portion 31. Further, the core wire 90 has a pressing member 92 near a proximal end of the guide wire port portion 33. Thus, when a pushing force and a rotating force are applied to the core wire 90, the pressing member 92 contacts the guide wire port portion 33, transmitting the pushing force and the rotating force to the distal end outer shaft portion 31 and the inner shaft 50A.

Below, the joining structure at the distal end 22A of the balloon 20A will be described with reference to FIGS. 2 to 3C.

Figure 2:
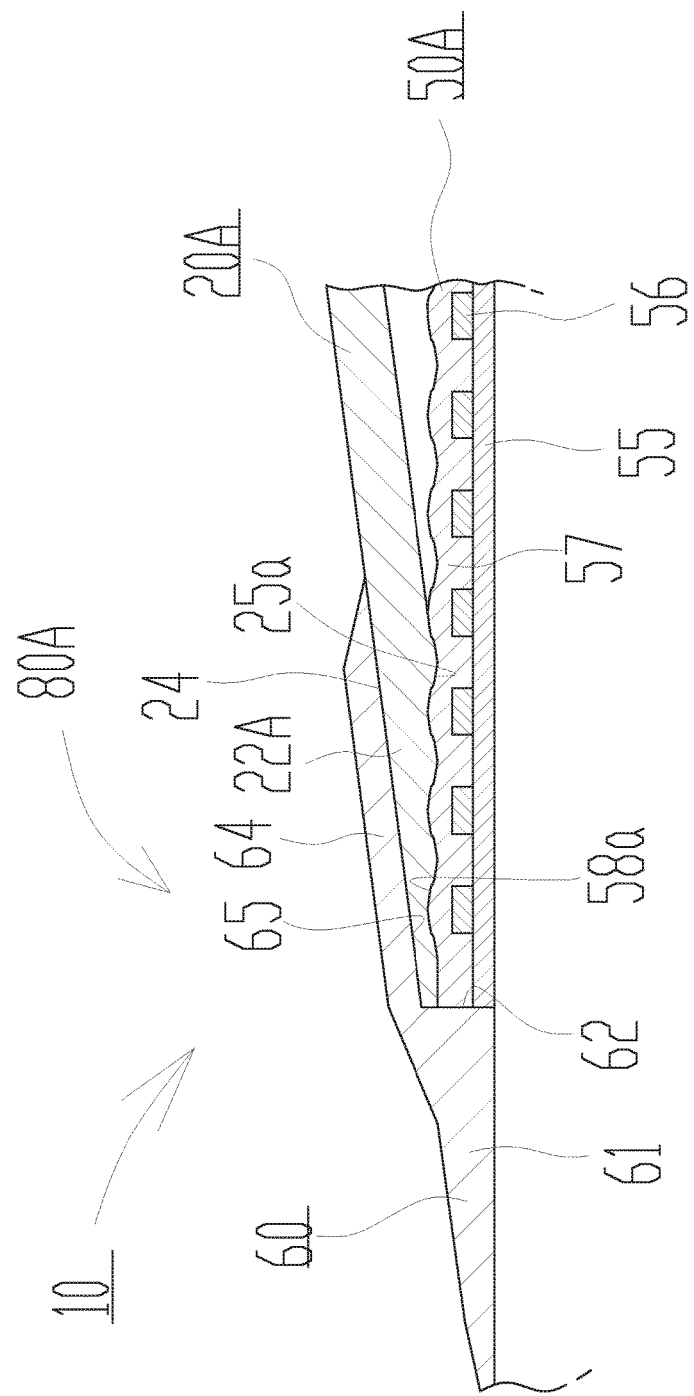
FIG. 2 shows an enlarged partial cross-sectional view of the balloon catheter shown in FIG. 1.

As shown in FIG. 2, the distal end 22A of the balloon 20A is sandwiched between the inner shaft 50A and the tip 60, joining the distal end 22A of the balloon 20A to the inner shaft 50A and the tip 60. According to the aforementioned joining structure, detachment of the distal end 22A of the balloon 20A from the inner shaft 50A can be prevented.

Figure 3A:
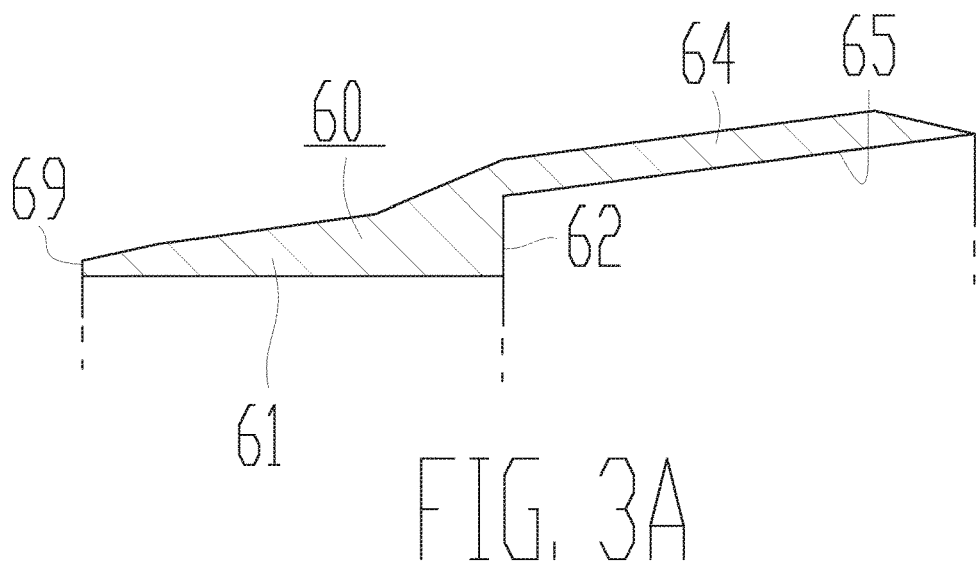
FIGS. 3A-3C show enlarged longitudinal sectional views of disassembled components of the balloon catheter of FIG. 1 (FIG. 3A: a tip.

More specifically, as shown in FIGS. 2 and 3A, an inner surface of the tip 60 includes a step portion 62 with which the distal end 22A of the balloon 20A and the distal end of the inner shaft 50A make contact. Further, the tip 60 comprises a tip distal end portion 61 having a tapered shape and extending from the step portion 62 toward the distal end guide wire port 69, and a tip proximal end portion 64 having a tapered shape and extending from the step portion 62 toward the proximal end. Note that an inner periphery of the tip proximal end portion 64 on the side of the inner shaft 50A corresponds to a tip proximal end joining inner surface 65.

Figure 3B:
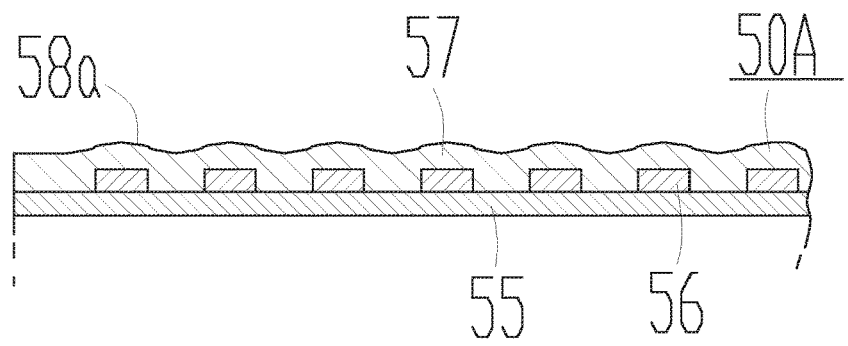

Furthermore, as shown in FIGS. 2 and 3B, the inner shaft 50A has a tubular inner layer 55, a metal coil body 56 sparsely wound around an outer periphery of the inner layer 55, and an outer layer 57 formed over the coil body 56. Moreover, the outer shape of the coil body 56 that is buried in the inner shaft 50A forms unevenness on an outer periphery 58a of the distal end of the inner shaft 50A.

Figure 3C:
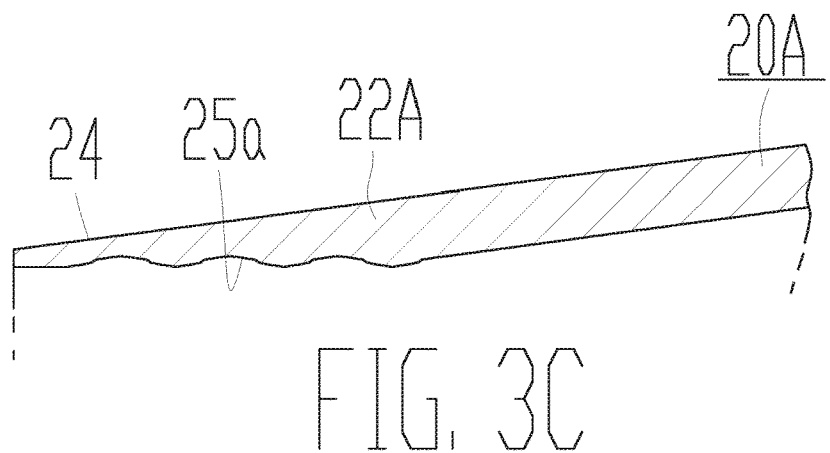

Further, as shown in FIGS. 2 and 3C, an inner periphery of the distal end 22A of the balloon 20A that faces the inner shaft 50A corresponds to a balloon distal end joining inner surface 25a, and the unevenness is formed on the balloon distal end joining inner surface 25a. In addition, the balloon distal end joining inner surface 25a is pre-formed so as to correspond to the unevenness on the outer periphery 58a of the distal end of the inner shaft 50A.

Further, as shown in FIG. 2, in a state where the distal end of the inner shaft 50A and the distal end 22A of the balloon 20A make contact with the step portion 62 of the tip 60, the balloon distal end joining inner surface 25a of the distal end 22A of the balloon 20A makes surface contact with the outer periphery 58a of the inner shaft 50A on which unevenness is formed, and the outer periphery 24 of the distal end 22A of the balloon 20A is covered with the tip proximal end portion 64 of the tip 60, and the distal end 22A of the balloon 20A, the inner shaft 50A, and the tip 60 are joined.

Here, a joining portion 80A corresponds to a portion where the distal end 22A of the balloon 20A, the inner shaft 50A, and the tip 60 are joined with each other. Therefore, even when a fluid is introduced into the inside of the balloon 20A to inflate the balloon 20A, and a stress is created for separating the distal end 22A of the balloon 20A from the distal end of the inner shaft 50A, detachment of the balloon 20A from the inner shaft 50A can be prevented because the distal end 22A of the balloon 20A is covered with the tip proximal end portion 64.

Further, the tip 60 is integrally formed from the tip distal end portion 61 of the distal end guide wire port 69 through the tip proximal end portion 64. Therefore, breakage and detachment of the tip 60 from the inner shaft 50A can be prevented.

Moreover, the joining portion 80A described above comprises the balloon 20A, the inner shaft 50A, and the tip 60, and other materials are not required. Therefore, the number of required components is minimized. Further, since the tip 60 (including the tip distal end portion 61 and the tip proximal end portion 64) has a tapered shape, the tip distal end portion 61 and the tip proximal end portion 64 can expand a stenosis site in a blood vessel in a radial direction when the balloon catheter 10 is inserted into the stenosis site. Further, the tip proximal end portion 64 covers the distal end 22A of the balloon 20A, reducing the risk of the balloon 20A getting damaged by contact with the stenosis site. As a result, when a fluid is introduced into the balloon 20A, there is a reduced a risk of the balloon 20A rupturing.

Further, since the balloon distal end joining inner surface 25a of the balloon 20A and the outer periphery 58a of the inner shaft 50A each have corresponding unevenness in surface contact with each other, the joining area is increased, obtaining an anchoring effect. Therefore, detachment of the distal end 22A of the balloon 20A from the inner shaft 50A can be much more effectively prevented.

The unevenness on the outer periphery 58a of the inner shaft 50A may be formed as follows: a molten resin is applied to the coil body 56 arranged on the inner layer 55, and then cured to form an outer layer 57 having unevenness. The unevenness is exposed on the outer periphery of the outer layer 57. Therefore, advantageously, an additional step for forming the unevenness is not required, and the number of manufacturing steps is minimized.

A joining portion 80B of a balloon catheter 11 of the disclosed embodiments will be described with reference to FIG. 4. Note that the same reference numbers are assigned to structures similar to those in the preceding figures, and the descriptions thereof are omitted.

Figure 4:
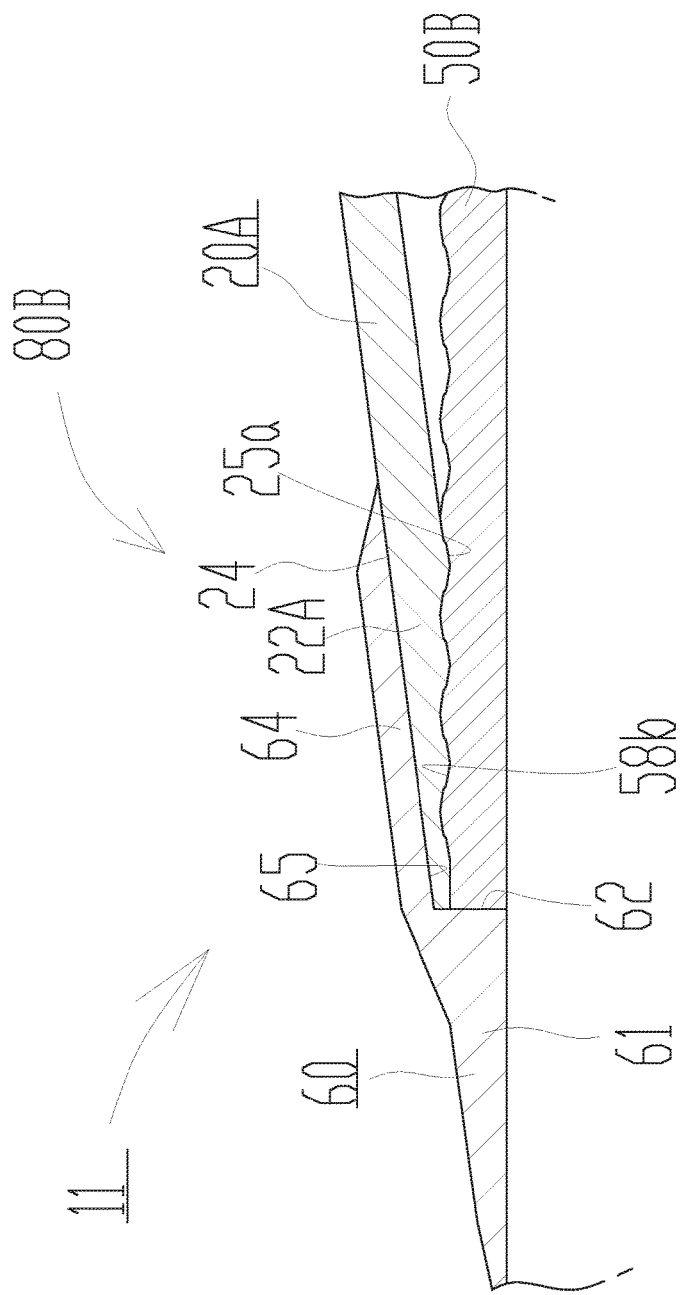
FIG. 4 shows an enlarged partial cross-sectional view of a balloon catheter according to the disclosed embodiments.

In FIG. 4, a monolayer inner shaft 50B is used instead of the inner shaft 50A of FIGS. 1, 2, and 3B, and the joining portion 80B comprises the tip 60, the distal end 22A of the balloon 20A, and the inner shaft 50B. Further, unevenness is formed on an outer periphery 58b of the inner shaft 50B. Therefore, again according to the aforementioned configuration, detachment of the distal end 22A of the balloon 20A from the inner shaft 50B; breakage and detachment of the tip 60 from the inner shaft 50B; and damage to the balloon 20A upon insertion into a stenosis site can be reduced without requiring additional components.

A joining portion 80C of a balloon catheter 12 according to the disclosed embodiments will be described with reference to FIG. 5. Note that the same reference numbers are assigned to structures similar to those in the preceding figures, and the descriptions thereof are omitted.

Figure 5:
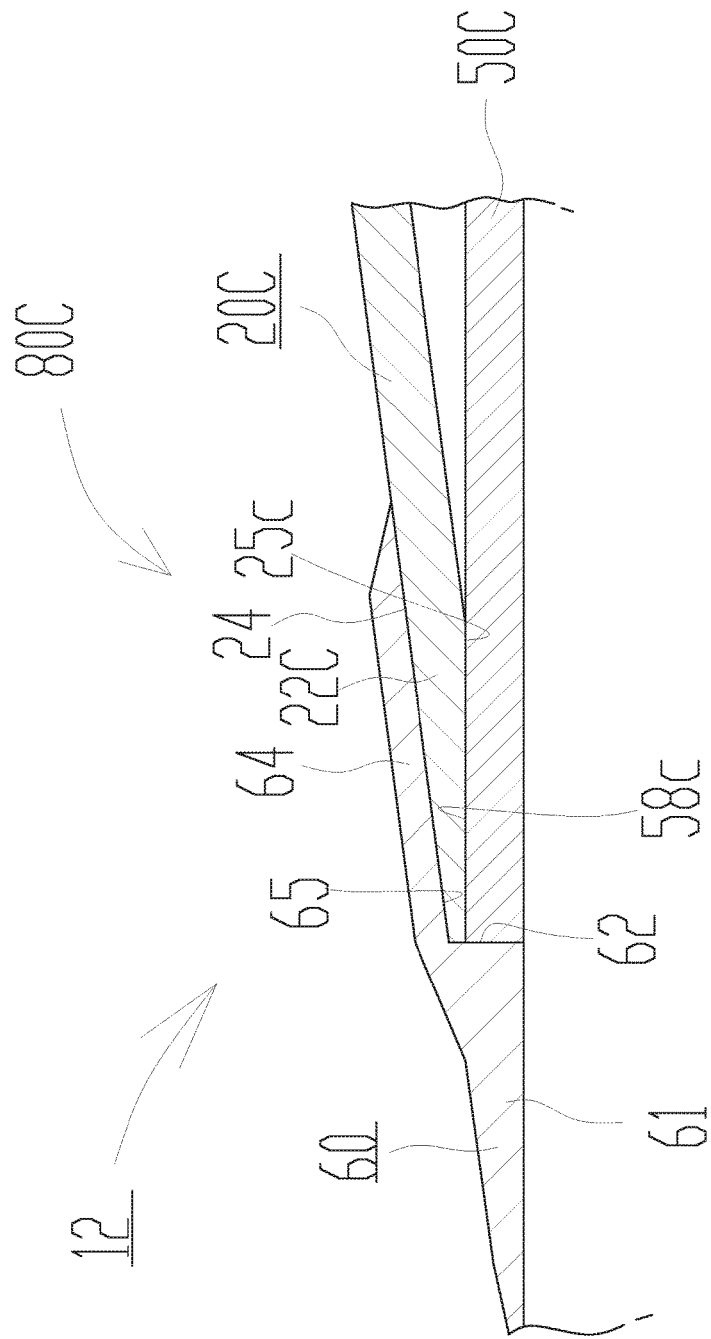
FIG. 5 shows an enlarged partial cross-sectional view of the balloon catheter shown in FIG. 4.

In FIG. 5, a monolayer inner shaft 50C is used instead of the inner shaft 50A used in FIGS. 1, 2, and 3B, and the joining portion 80C comprises the tip 60, a distal end 22C of a balloon 20C, and the inner shaft 50C. Further, an outer periphery 58c of the inner shaft 50C is formed so as to have a smooth surface without unevenness. A balloon distal end joining inner surface 25c of the balloon 20C is also formed so as to have a smooth surface without unevenness. Even with the smooth surface, detachment of the distal end 22C of the balloon 20C from the inner shaft 50C; breakage and detachment of the tip 60 from the inner shaft 50C; and damage to the balloon 20C upon insertion into a stenosis site can be reduced without requiring additional components.

Note that other modifications can be made to the disclosed embodiments in addition to as the modifications described above. For example, the unevenness on the outer periphery 58a, 58b of the inner shaft 50A, 50B is not limited to a coil-like unevenness corresponding to the shape of the coil body 56 wound sparsely. The unevenness may be embossed such that a depressed portion and a protruding portion are provided at a given interval, or the unevenness may be intermittently formed along the axial direction of the inner shaft 50A, 50B. Further, the unevenness on the outer periphery 58a of the inner shaft 50A may be formed from the coil body 56 that is completely buried in the inner shaft 50A, but the configuration is not limited to this. For example, (a) the outer periphery of the coil body 56 may be partially exposed at the outer periphery 58a of the inner shaft 50A so that both the coil body 56 and the outer layer 57 form unevenness on the outer periphery 58a of the inner shaft 50A, or (b) the unevenness on the outer periphery 58a of the inner shaft 50A may be formed from the coil body 56 and the inner layer 55 without using the outer layer 57.

Further, in the balloon catheter 10, 11, 12, a wide range of dimensions and shapes may be suitably selected for each component. Therefore, for example, the length of the tip proximal end portion 64 of the tip 60 along the axial direction of the tip 60, the thickness of the tip 60 in the radial direction, and the like can be freely adjusted, thereby optimizing the joining strength between the tip 60, the distal end 22A, 22C of the balloon 20A, 20C, and the inner shaft 50A, 50B, 50C.

Further, in FIGS. 2 and 3B, the coil body 56 having a rectangular cross-sectional shape is wound around the outer periphery of the inner layer 55, but the configuration is not limited to this. The cross-sectional shape of a wire of the coil body 56 may be circular, elliptical, or polygonal. Further, the wire of the coil body 56 is not limited to a metal wire, and a wire comprising a resin such as polyether ether ketone (PEEK) may also be used. Furthermore, a braid in which multiple wires are woven in a mesh-like manner may also be used instead of the coil body 56.

What is claimed is:
1. A balloon catheter comprising:
   a balloon;
   an outer shaft;
   an inner shaft joined to a distal end of the balloon and comprising a coil body; and
   a tip having:
      a step portion provided on an inner surface thereof and configured to come in contact with a distal end of the inner shaft; and
      a proximal end portion that covers an outer periphery of the distal end of the balloon, wherein:
the distal end of the balloon is sandwiched between the inner shaft and the proximal end portion of the tip,
an outer periphery of the inner shaft has an uneven surface topography, corresponding to the shape of the coil body, at a joining portion in which the distal end of the balloon, the inner shaft, and the tip are joined, and
an inner periphery of the distal end of the balloon at the joining portion has an uneven surface topography corresponding to the uneven surface topography of the outer periphery of the inner shaft.

2. A balloon catheter comprising:
a balloon;
an outer shaft;
an inner shaft joined to a distal end of the balloon and comprising a coil body that is partially buried inside the inner shaft and partially exposed; and
a tip having:
   a step portion provided on an inner surface thereof and configured to come in contact with a distal end of the inner shaft; and
   a proximal end portion that covers an outer periphery of the distal end of the balloon,
wherein:
the distal end of the balloon is sandwiched between the inner shaft and the proximal end portion of the tip, and
an outer periphery of the inner shaft has an uneven surface topography, corresponding to the shape of the coil body, at a joining portion in which the distal end of the balloon, the inner shaft, and the tip are joined.

3. A balloon catheter comprising:
a balloon;
an outer shaft;
an inner shaft joined to a distal end of the balloon and comprising a coil body; and
a tip joined to a distal end of the inner shaft and having a proximal end portion that covers an outer periphery of the distal end of the balloon,
wherein:
the distal end of the balloon is sandwiched between the inner shaft and the proximal end portion of the tip,
an outer periphery of the inner shaft has an uneven surface topography corresponding to the shape of the coil body at a joining portion in which the distal end of the balloon, the inner shaft, and the tip are joined, and
an inner periphery of the distal end of the balloon at the joining portion has an uneven surface topography corresponding to the uneven surface topography of the outer periphery of the inner shaft.

4. A balloon catheter comprising:
a balloon;
an outer shaft;
an inner shaft joined to a distal end of the balloon and comprising a coil body that is partially buried inside the inner shaft and partially exposed; and
a tip joined to a distal end of the inner shaft and having a proximal end portion that covers an outer periphery of the distal end of the balloon,
wherein:
the distal end of the balloon is sandwiched between the inner shaft and the proximal end portion of the tip, and
an outer periphery of the inner shaft has an uneven surface topography corresponding to the shape of the coil body at a joining portion in which the distal end of the balloon, the inner shaft, and the tip are joined.

* * * * *